United States Patent
Ford et al.

(10) Patent No.: US 10,150,723 B2
(45) Date of Patent: Dec. 11, 2018

(54) SEPARATION OF ENANTIOMERS OF 3-ETHYLBICYCLO[3.2.0]HEPT-3-EN-6-ONE

(71) Applicant: Novassay S.A., Epalinges (CH)

(72) Inventors: Rhonan Lee Ford, Ongar (GB); Premji Meghani, Loughborough (GB)

(73) Assignee: Novassay S.A., Epalinges (CH)

( * ) Notice: Subject to any disclaimer, the term of this patent is extended or adjusted under 35 U.S.C. 154(b) by 0 days.

(21) Appl. No.: 15/576,720

(22) PCT Filed: Feb. 2, 2016

(86) PCT No.: PCT/EP2016/052176
§ 371 (c)(1),
(2) Date: Nov. 23, 2017

(87) PCT Pub. No.: WO2016/146299
PCT Pub. Date: Sep. 22, 2016

(65) Prior Publication Data
US 2018/0134643 A1    May 17, 2018

Related U.S. Application Data

(60) Provisional application No. 62/167,232, filed on May 27, 2015.

(51) Int. Cl.
| | | |
|---|---|---|
| C07C 45/85 | (2006.01) | |
| C07D 257/04 | (2006.01) | |
| C07B 57/00 | (2006.01) | |
| A61P 25/00 | (2006.01) | |
| C07B 43/02 | (2006.01) | |
| C07B 43/08 | (2006.01) | |
| C07B 63/02 | (2006.01) | |
| C07C 49/627 | (2006.01) | |
| C07D 207/06 | (2006.01) | |
| C07D 211/32 | (2006.01) | |

(52) U.S. Cl.
CPC ............ C07C 45/85 (2013.01); A61P 25/00 (2018.01); C07B 43/02 (2013.01); C07B 43/08 (2013.01); C07B 57/00 (2013.01); C07B 63/02 (2013.01); C07C 49/627 (2013.01); C07D 257/04 (2013.01); C07C 2602/20 (2017.05); C07D 207/06 (2013.01); C07D 211/32 (2013.01)

(58) Field of Classification Search
CPC .... C07C 45/85; C07D 257/04; C07D 207/06; C07D 211/32; C07B 43/02; C07B 43/08
See application file for complete search history.

(56) References Cited

U.S. PATENT DOCUMENTS

| | | | | |
|---|---|---|---|---|
| 9,663,479 B2* | 5/2017 | Meghani | ............. | C07D 257/04 |
| 2012/0071685 A1* | 3/2012 | Kitagawa | ............. | A61K 31/195 560/119 |
| 2014/0296569 A1* | 10/2014 | Nakamura | ............. | C07C 45/85 562/501 |

FOREIGN PATENT DOCUMENTS

EP          0074856 A2 *   3/1983   ............. C07C 45/64

* cited by examiner

*Primary Examiner* — Sikarl A Witherspoon
(74) *Attorney, Agent, or Firm* — Matthew Kaser; Adam Warwick Bell

(57) ABSTRACT

A process to isolate a compound of Formula (2a) or a salt or solvate thereof, comprising a) reacting a mixture of diastereoisomers of Formulae (2a, 2b) with a basic heterocyclic-aldehyde compound and an optically active amine in the presence of a base; and b) separating the compound of Formula (2a) from the product of step a) by acid extraction. The compound of Formula (2a) may be produced with an enantiomeric excess of 98%. Compounds of Formula (2a) are useful intermediates in a process to prepare a bicyclic γ-amino tetrazole derivative of Formula (I) which finds utility in treating neuropathic pain and disorders of the central nervous system.

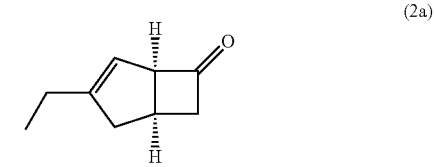

(2a)

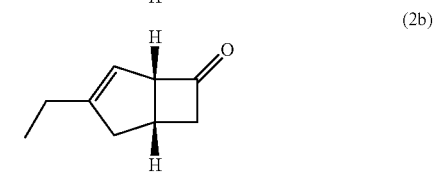

(2b)

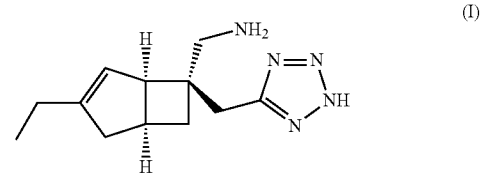

(I)

23 Claims, No Drawings

SEPARATION OF ENANTIOMERS OF 3-ETHYLBICYCLO[3.2.0]HEPT-3-EN-6-ONE

This application claims priority to and benefits under 35 U.S.C. § 371 of International Patent Application Serial Number PCT/EP2016/052176, filed 2 Feb. 2016, entitled "Separation of Enantiomers of 3-Ethylbicylo[3.2.0]hept-3-en-6-one" which claimed the benefit under 35 U.S.C. § 119(e) of U.S. Provisional Application Ser. No. 62/167,232, filed 27 May 2015, entitled "Method for producing a bicyclic γ-amino tetrazole derivative", the contents of which are all incorporated by reference in their entirety for all purposes into the present disclosure.

TECHNICAL FIELD

The present invention relates to a production method for an optically active intermediate compound useful in the preparation of an optically active bicyclic γ-amino tetrazole derivative or a pharmacologically acceptable salt thereof, particularly a compound having activity as an $α_2δ$ ligand, and to the production of the tetrazole derivative.

BACKGROUND ART

Voltage-gated calcium channels are formed by combinations of the pore-forming $α_1$ subunit and auxiliary proteins $α_2δ$, β, and γ (Caterall (2000) Annu. Rev. Cell Dev. Biol. 16:521-555). The $α_2δ$ protein is known to regulate both calcium channel density and the voltage-dependent kinetics of these channels (Felix et al (1997) J. Neuroscience 17: 6884-6891; Klugbauer et al (1999) J. Neuroscience 19:684-691; Hobom et al (2000) Eur. J. Neuroscience 12:1217-1226; and Qin et al (2002) Mol. Pharmacol. 62:485-496).

Gabapentin (GBP) is an anti-epileptic, anti-hyperalgesic and anxiolytic drug which binds with high affinity to two sub-types of calcium channel $α_2δ$ subunits $α_2δ_1$ and $α_2δ_2$. GBP was originally developed for epilepsy and has also found application in the treatment of pain and anxiety (Taylor et al (1998) Epilepsy Res. 29:223-249). The mechanism underlying GBP's action is still poorly understood. GBP was originally designed as a lipophilic γ-amino butyric acid (GABA) analogue, but has subsequently been shown not to interact with any of the enzymes on the GABA metabolic pathway, nor does it interact directly with the $GABA_A$ or $GABA_B$ receptors. However, it is able to efficiently cross the blood brain barrier via an L-system amino acid transporter.

Pregabalin (PGB) is a second generation, more potent, successor to GBP for the treatment of the same conditions as those listed above. GBP (Structure GBP, below) and PGB (Structure PGB, below) bind to the $α_2δ$-1 sub-unit with $IC_{50}$ values of 140 and 80 nM, respectively (Dolphin (2013) Bioch Biophys Acta 1828: 1541-1549).

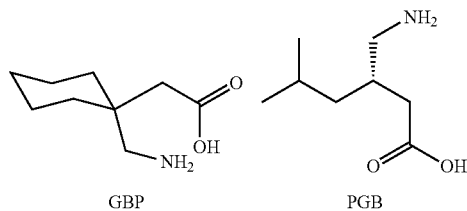

GBP   PGB

GBP shows few, if any, toxic side effects at clinically-relevant doses. It does, however, possess a relatively short half-life, being excreted unchanged, possibly due to very high water solubility and apparent lack of protein binding in vivo. Mild sedation, dizziness and ataxia are the main dose-limiting side effects and these are believed to be centrally-mediated.

GBP and PGB, unlike many other centrally-acting drugs, are hydrophilic and doubly-charged at neutral pH, making them insoluble in lipids, such as cell membranes. However, both compounds appear to cross membrane barriers of the gut, blood-brain barrier and cell membranes via a specialised transporter system (system L) that also transports endogenous amino acids, such as L-leucine, L-isoleucine and L-valine (Su et al (2005) J. Pharm. Exp. Ther. 313, 1-10).

In mammals, there are four related sub-types of the $α_2$ protein, each coded by a different gene. Each protein sub-type has a molecular weight of approximately 150 kiloDaltons (kD) and consists of 997-1150 amino acid residues. Only $α_2δ$ sub-types 1 and 2 bind PGB with high affinity; sub-types 3 and 4 are devoid of significant drug binding (Fink et al (2002) Neuropharmacology, 42, 229-236). The binding affinity of PGB is similar for recombinant $α_2δ$ type 1 and type 2 proteins, demonstrating that PGB is not sub-type selective (Piechan et al (2004) Soc. Neuroscience Abstr., 111 (program No 115)).

WO 2015/091463 discloses inter alia a bicyclic γ-amino tetrazole derivative of Formula 1, Formula 1 useful in the treatment of pain, and production methods therefor.

US 2012/0071685 relates to the production of bicyclic γ-amino acid derivatives having activity as a $α_2$ ligand and intermediates thereof, including the synthesis of a diastereomeric mixture of compounds of Formulae 2a, 2b.

Formula 2a

Formula 2b

However, this diastereoisomeric mixture 2a, 2b is not resolved into individual isomers.

US 2014/0094623 discloses a 3-step method to produce a compound of Formula A and a compound of Formula B from a mixture thereof

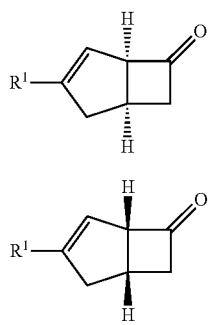

Formula A

Formula B by (a) reacting a bis-allylic acetal with an acid or acid anhydride and an acid to produce an aldehyde by Claisen rearrangement, (b) heating the product of stage (a) with malonic acid to produce an alpha-beta unsaturated acid and (c) heating the product of stage (b) with an acid anhydride and a tertiary amine to produce the 4-5 bicyclic ring system by a [2+2] cycloaddition reaction. The separation of above-identified compounds of Formula A or Formula B from a diastereoisomeric mixture thereof is also described in US 2015/0038738, which discloses an enzymatic method to separate the compounds, and in US 2014/0296569, which utilises a reaction of the diastereoisomeric mixture with an acidic benzaldehyde reagent, an optically active amine and a solvent.

SUMMARY OF THE INVENTION

(I) Technical Problem

An object of the present invention is to provide a production method for a bicyclic γ-amino tetrazole derivative of Formula 1

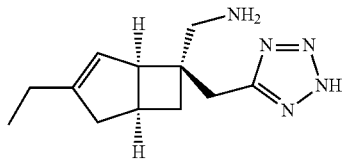

Formula 1 having excellent activity as an $\alpha_2$ ligand and an intermediate for producing the same, and pharmacologically acceptable salts thereof.

In a previous production method, the compound of Formula 1 was prepared in seven synthetic steps from racemic ketone of Formulae 2a & 2b with additional optical resolution performed as the final step by use of chiral high performance liquid chromatography (HPLC) as shown in Scheme 1 (see WO 2015/091463 and US 2012/0071685).

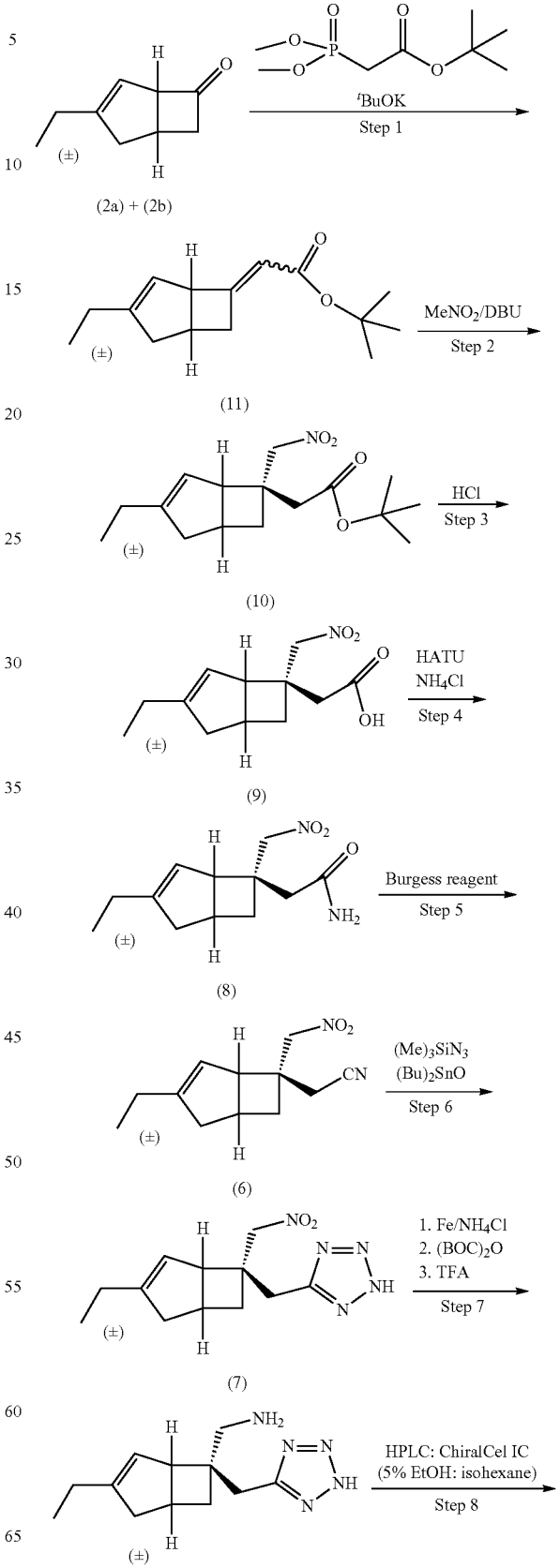

Scheme 1

-continued

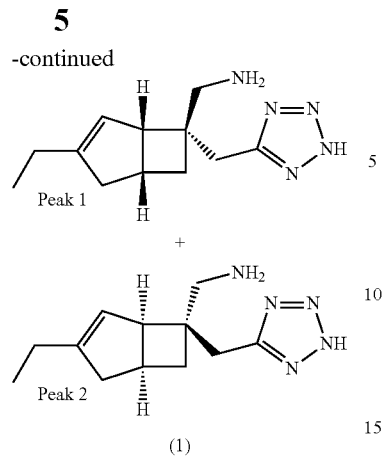

(1)

(II) Solution to the Problem

A technical problem to be solved by the present invention is to develop a production method which involves preparing an intermediate compound in the preparation of compounds of Formula 1, as an optically active compound, in an earlier step, followed by fewer synthetic transformations, in the production of a compound of Formula 1.

The present inventors, however, have hypothesized that a more efficient production method would be established by carrying out the optical resolution in an earlier step and use of subsequent synthetic transformations that more efficiently produce a compound of Formula 1. By this method, it is possible to produce a compound of Formula 1 in four overall synthetic steps.

The invention will be described below. The method produces the compound of Formula 1 or a salt thereof by optical kinetic resolution performed early in the synthetic sequence. Focusing on a stereocontrol method for an asymmetric carbon in the method for producing a compound of Formula 2a, the present inventors have continued diligent studies to develop an efficient method thereof. The present inventors have found that such method to produce a compound of Formula 2a is of value in a process to prepare a compound of Formula 1 as shown by Scheme 2.

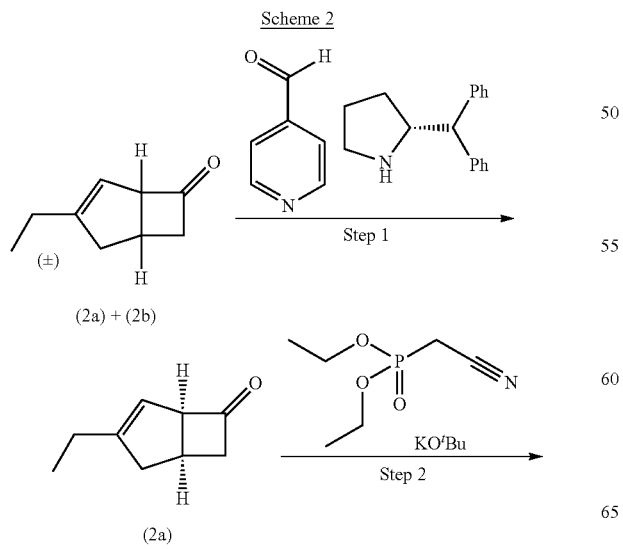

-continued

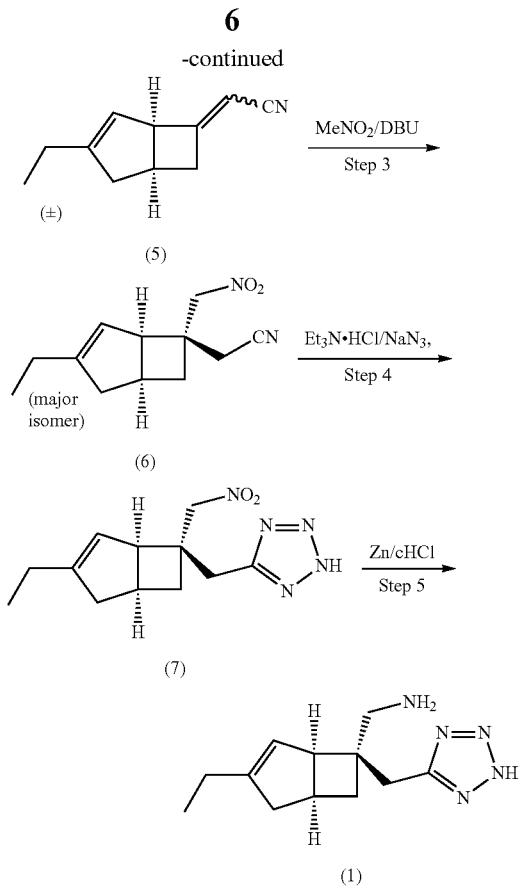

Accordingly, the present invention provides a process to isolate a compound of Formula 2a

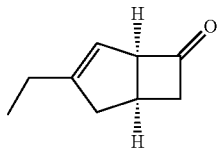

Formula 2a or a salt or solvate thereof, comprising
a) reacting a mixture of diastereoisomers of Formulae 2a,2b

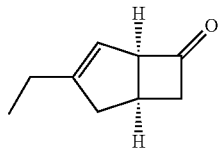

Formula 2a

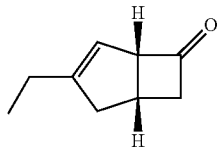

Formula 2b with a basic heterocyclic-aldehyde compound in the presence of an optically active amine and a base; and b) separating the compound of Formula 2a from the product of step a) by acid extraction.

The process may produce the compound of Formula 2a with an enantiomeric excess greater than 90%, preferably greater than 95% and more preferably greater than 98%.

Preferred aspects of the present invention will be described below.

The method comprises reacting a mixture of diastereoisomers of Formulae 2a and 2b,

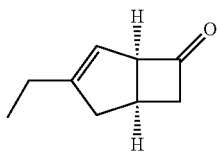
Formula 2a

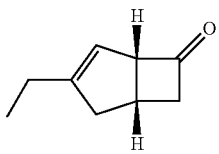
Formula 2b especially a racemic mixture of compounds of Formulae 2a and 2b, with a basic heterocyclic-aldehyde compound in the presence of an optically active amine and a base. In the process according to the invention, it is believed that the compound of Formula 2b reacts with the basic heterocyclic-aldehyde compound in the presence of an optically active amine to produce heterocyclic aryl derivatives, whereas the compound of Formula 2a remains unreacted. The compound of Formula 2a may easily be separated by conventional acid extraction techniques.

The basic heterocyclic-aldehyde compound is preferably a compound of Formula 12

Formula 12 in which Ar represents a heterocyclic 5- or 6-membered heteroaryl ring structure, optionally substituted by one or two substituents selected from $C_{1-6}$ alkyl and $C_{1-6}$ alkoxy. Preferably, Ar represents an imidazolyl or pyridyl ring structure. Typical examples include, but are not limited to, compounds such as 1-methyl-5-imidazolecarboxaldehyde, 1-methyl-4-imidazolecarboxaldehyde, 3-pyridinecarboxaldehyde and 2-pyridinecarboxaldehyde. Further preferably, the basic heterocyclic-aldehyde compound is a compound of Formula 13

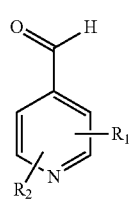
Formula 13 in which $R_1$ represents hydrogen or $C_{1-6}$ alkyl and $R_2$ represents hydrogen or $C_{1-6}$ alkoxy, such as 4-pyridinecarboxyaldehyde. When the reaction is carried out with a compound of Formula 13, the compound of Formula 2b is converted into adducts denoted by a mixture of compounds Formula 14 (depicted by Formulae 3 and 4 in Scheme 3 below).

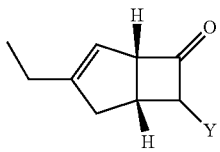
Formula 14 in which Y represents =CH-(4-pyridyl) or —CH(OH)-(4-pyridyl).

Thereafter, compounds of Formula 14 may be efficiently separated from unreacted compound of Formula 2a by acidic partition phase separation techniques as illustrated in Scheme 3. The separation process is conveniently conducted with compounds of Formula 13 as the basic pyridine functionality facilitates separation, particularly in the case where the optically active amine comprises (R)-2-(diphenylmethyl)pyrrolidine and the base comprises 4-methylmorpholine.

Preferably, in a process according to the present invention, the stoichiometric ratio of the basic heterocyclic-aldehyde compound to the mixture of diastereoisomers of Formulae 2a, 2b is in the range 0.5:1 to 2:1, more preferably in a ratio of 1:1. Typically, the reaction between the mixture of diastereoisomers of Formulae 2a, 2b, the basic heterocyclic-aldehyde compound and the optically active amine is conducted over a period of up to 24 hours, generally in the range 15 to 24 hours, at a temperature in the range from ambient to 80° C., more particularly 30 to 60° C. In a preferred embodiment, the reaction is conducted at 35 to 45° C. over a period of 15 to 20 hours.

Suitably, the optically active amine is a secondary amine. Typical examples of the optically active amine include, but are not limited to, (R,R)-2,5-bis(methoxymethyl)-pyrrolidine, (R)-(2-pyrrolidinyl)-1H-tetrazole, (R)-2-(methoxymethyl)pyrrolidine, (R)-2-(ethoxymethyl)pyrrolidine, (R)-2-(isopropoxymethyl)pyrrolidine, (R)-2-(t-butoxymethyl)pyrrolidine, (R)-2-(phenoxymethyl)pyrrolidine, (R)-2-(diphenylmethyl)-pyrrolidine, N-[(2R)-2-pyrrolidinylmethyl]-trifluoromethanesulfonamide, (R)-2-[bis(4-methylphenyl)methyl]pyrrolidine, (R)-2-[bis(3,5-dimethylphenyl)methyl]pyrrolidine, (R)-2-[bis(4-fluorophenyl)methyl]pyrrolidine, and (S)-4,5-dihydro-3H-dinaphtho[2,1-c:1',2'-e]azepine-2,6-diylbis(diphenylmethanol). Preferred optically active amines include (R)-2-(diphenylmethyl)pyrrolidine, (R)-2-[bis(4-methylphenyl)methyl]pyrrolidine, (R)-2-[bis(3,5-dimethylphenyl)methyl]pyrrolidine and (R)-2-[bis(4-fluorophenyl)methyl]pyrrolidine. A particular preferred optically active amine is (R)-2-(diphenylmethyl)pyrrolidine.

Preferably, the stoichiometric ratio of the optically active amine to the mixture of diastereoisomers of Formulae 2a, 2b is in the range 0.01:1 to 1:1, more preferably in a range of 0.01:0.3.

Typical examples of the base include, but are not limited to, 4-methylmorpholine, N,N-diisopropylethylamine, triethylamine, tributylamine, N-methylpyrrole, N-methylpyrolidine, N-methylpiperadine, pyridine, 4-picoline, 2,6-lutidine, N-methylimidazole, N,N-diethylaniline, potassium phosphate, 1,8-diazobicyclo[5,4,0]undec-7-ene and 1,4-diazobicyclo[2,2,2]octane. A preferred base is 4-methylmorpholine. Preferably, the stoichiometric ratio of the base to the mixture of diastereoisomers of Formulae 2a, 2b is in the range 0.5:1 to 1:1.5, more preferably in a range of 0.8:1 to 1:1.3.

The reaction may advantageously be carried out in the presence of the solvent, particularly a polar solvent. Typical examples include, but are not limited to, 1-methyl-2-pyrrolidinone, N,N-dimethylformamide, N,N-dimethylacetamide, acetonitrile, 2-propanol, tetrahydrofuran, 1,2-dimethoxyethane and dimethylsulfoxide. A particularly preferred solvent is 1-methyl-2-pyrrolidinone.

In a further preferred aspect of the present invention, the basic heterocyclic-aldehyde compound, the base and the optically active amine are separated from unreacted compound of Formula 2a by acid phase extraction. In a particularly preferred aspect of the present invention, 4-methylmorpholine (base), any unreacted 4-pyridinecarboxyaldehyde (basic heterocyclic-aldehyde) and remaining (R)-2-(diphenylmethyl)pyrrolidine (optically active amine) are separated from unreacted compound of Formula 2a by acid phase extraction. Typically, the acid extraction is carried out with an aqueous solution of an acid, for example hydrochloric acid, sulphuric acid, phosphoric acid, citric acid, oxalic acid or tartaric acid at ambient temperature. Suitably, the acid extraction is carried out with hydrochloric acid or sulphuric acid in the presence of a solvent and water. Examples of solvent include diethyl ether, t-butylmethylether, ethyl acetate, 2-methyltetrahydrofuran, isohexane, dichloromethane. After agitation and allowing for phase separation, the phase containing the compound of Formula 2a is collected. In a preferred embodiment, the reaction mixture is washed with hydrochloric acid (typically 1M), water and brine and diethyl ether. The aqueous layer may be further washed with isohexane and a further sample of compound of Formula 2a collected.

A preferred embodiment of the invention may be depicted by Scheme 3 below.

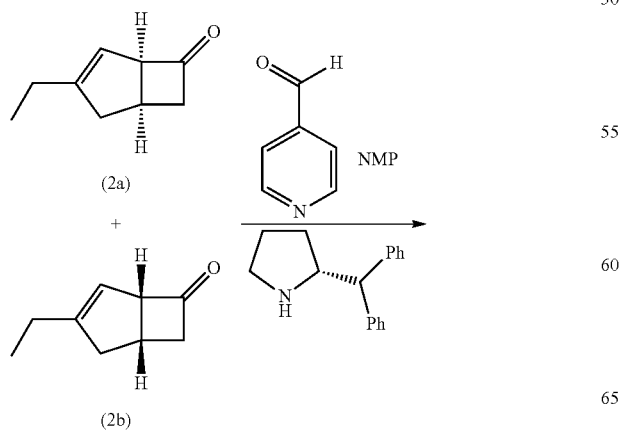

Scheme 3

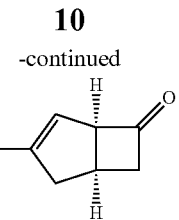
(2a)

+

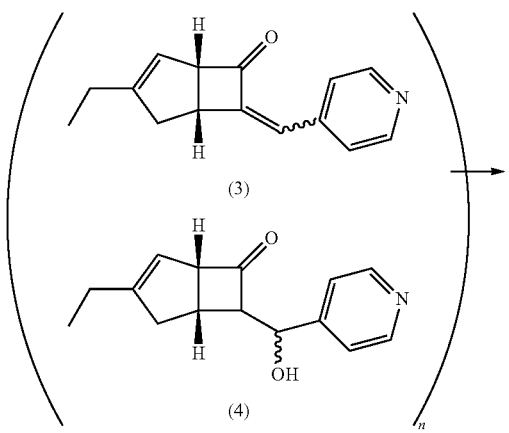

Removed by acidic phase extraction

In a further aspect of the invention, there is provided a process to prepare a compound of Formula 1

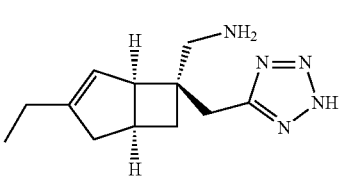

Formula 1 or a pro-drug thereof, comprising the step of resolving a mixture of diastereoisomers of Formulae 2a, 2b

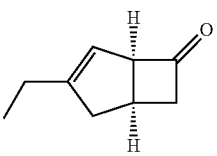

Formula 2a

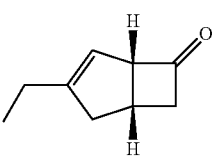

Formula 2b into a compound of Formula 2a

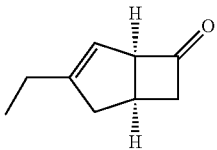

Formula 2a by reaction with a basic heterocyclic-aldehyde compound in the presence of an optically active amine and a base and separating out the compound of Formula 2a, followed by conversion of a compound of Formula 2a to a compound of Formula 1.

In a preferred embodiment, said conversion comprises reacting a compound of Formula 2a

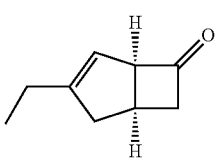

Formula 2a with a double bond-forming reagent in the presence of a base to prepare a compound of Formula 5

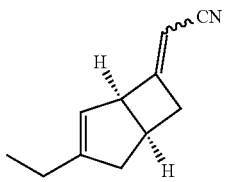

Formula 5

Preferably, a suitable double bond-forming reagent comprises, for example, diethyl cyanomethylphosphate, and a suitable base comprises, for example, potassium tert-butoxide. The reaction is conveniently carried out in a suitable solvent, for example tetrahydrofuran, at a temperature in the range 0° C. to ambient temperature.

Said conversion may further comprise reacting a compound of Formula 5

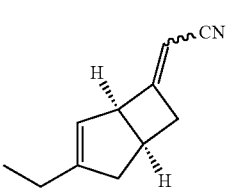

Formula 5 with nitromethane in the presence of a base to prepare a compound of Formula 6

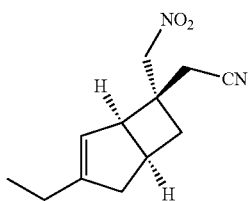

Formula 6

Said conversion may further comprise reacting a compound of Formula 6

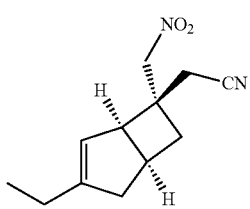

Formula 6 with an azide compound, eg a ring forming reaction, optionally in the presence of a catalyst and at elevated temperature, to prepare a compound of Formula 7

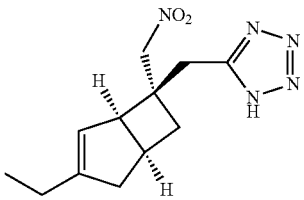

Formula 7

A suitable azide may be, for example, sodium-, potassium- or trimethylsilyl-azide together with commonly known suitable catalysts such a dibutyltin oxide, pyridine hydrochloride, triethylamine hydrochloride or ammonium chloride in a solvent such as dimethylformamide (DMF), N-methyl-2-pyrrolidinone (NMP) or toluene. The reaction may be conducted at elevated temperatures ranging from 60° C. to 120° C.

Said conversion may further comprise reducing a compound of Formula 7

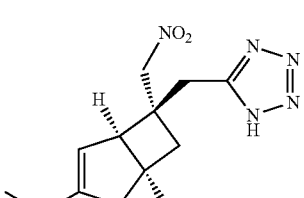

Formula 7 to prepare the compound of Formula 1

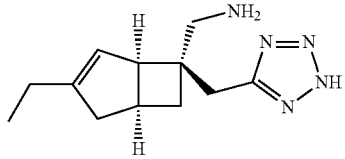

Formula 1

Suitable reducing agents include using a mixture of suitable metals such, zinc, iron or tin in the presence of a suitable acid and solvent such as hydrochloric acid, sulphuric acid, acetic acid or ammonium chloride in water or ethanol at 0° C. to ambient temperatures. Alternatively, suitable reducing agents include hydrazine hydrate in the presence of a metal such as Raney Nickel in a suitable solvent such as mixtures of ethanol and water. A preferred embodiment includes using zinc and concentrated hydrochloric acid at temperatures between 0° C. and 35° C.

Advantageously, the pro-drug may be a hydrolysable carbamate of the amine group of compounds of Formula 1.

In a further aspect, the present invention provides a process to prepare compounds of Formula 14

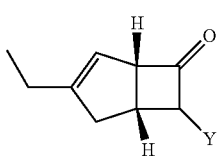

Formula 14 in which Y is =CH-(4-pyridyl) or —CH(OH)-(4-pyridyl), the process comprising treating mixture of diastereoisomers of Formulae 2a, 2b

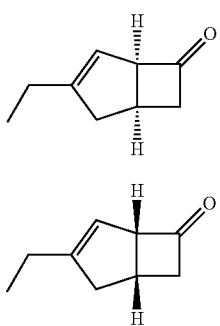

Formula 2a

Formula 2b with a basic heterocyclic-aldehyde compound of Formula 13

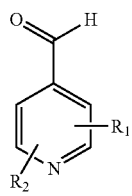

as described above
in the presence of an optically active amine and a base.

Advantageous Effects of Invention

The production method according to the present invention can provide a bicyclic γ-amino tetrazole derivative of Formula 1 having excellent activity as an $\alpha_2\delta$ ligand, an intermediate for producing the same, or salts thereof. Furthermore, basic heterocyclic-aldehydes such as 4-pyridinecarboxaldehyde react with the unwanted isomer of Formula 2b to produce basic derivatives, for example of Formula 14 in which Y is =CH-(4-pyridyl) or —CH(OH)-(4-pyridyl), that are efficiently removed by acidic phase separation techniques to produce the desired compound of Formula 2a with enantiomeric excess (ee) ≥98% as summarised in Scheme 3. Subsequent modification in four synthetic steps provides a compound of Formula 1 as summarised in Scheme 2.

DESCRIPTION

As used herein, the term "compound of Formula 1" includes pharmaceutically acceptable salts and solvates thereof. References to the intermediate compounds also include salts and solvates thereof. Pharmaceutically acceptable salts of the compounds of the invention may include basic addition salts of the compound. Such salts may be formed with an inorganic base which affords a pharmaceutically acceptable cation, for example, an alkali metal salt, such as a sodium or potassium salt, or an alkaline earth metal salt such as a calcium or magnesium salt. Pharmaceutically acceptable salts of the invention may also include acid addition salts. Such salts may be formed with an inorganic or organic acid which affords a pharmaceutically acceptable anion, for example a hydrohalide salt, such as a chloride or bromide salt, a sulphate or phosphate salt, or an organic acid salt, for example a salt with acetate, fumarate, maleate, tartrate, lactate, citrate, pyruvate, succinate, oxalate, methanesulphonate or p-toluenesulphonate. The term "solvate" refers to a compound of the invention in the solid state, wherein molecules of a suitable solvent are incorporated in the crystal lattice. A suitable solvent for therapeutic administration is physiologically acceptable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Typical solvates include hydrates such as the monohydrate, dihydrate or trihydrate.

The present invention further relates to a process to prepare pro-drugs of a compound of Formula 1, for example in vivo hydrolysable carbamates on the amino functionality of compound of Formula 1. An in vivo hydrolysable carbamate of a compound of Formula 1 which contains carboxy, ether, or hydroxy groups is, for example, a pharmaceutically acceptable carbamate which is cleaved in the human or animal body to produce the parent amine. Such carbamates can be identified by administering, for example, intravenously to a test animal, the compound under test and subsequently examining the test animal's body fluid.

Typical pharmaceutical compositions comprise a therapeutically effective amount of a compound of Formula 1 together with a pharmaceutically acceptable carrier. The compound of Formula 1 is used in an amount effective to treat, reduce or ameliorate neuropathic pain in a subject, especially a human subject suffering from a painful condition. Such treatment of pain may or may not be associated with a central nervous system (CNS) or peripheral nervous system (PNS) disorder. The compound of Formula 1 is also effective to treat, reduce or ameliorate any other non-pain related CNS disorders.

The compositions comprise a therapeutically effective amount of the compound of Formula 1, which is generally in the range 0.1-95% w/w of the compound of Formula 1, but is dependent on the precise nature of the active and the mode of administration. Typically, the dose of active is in the range 0.1 to 500 mg as single or divided doses, depending on the precise nature of the active and the mode of administration.

In therapeutic use, the compound of Formula 1 may be administered orally, rectally, parenterally, or topically. The pharmaceutical compositions may take the form of any oral, rectal, parenteral or topical composition known to those skilled in the art, using carriers well known in the art of pharmacy. Such compositions are generally prepared in unit dosage form. Compositions for oral administration may include solid dosage forms, such as tablets, capsules or caplets, or liquid dosage forms, such as syrups and aqueous or oily suspensions. Solid dosage forms such as tablets and caplets may be prepared by mixing a compound of Formula 1 with an inert diluent in the presence of disintegrating agents and other formulation aids such as lubricants. Capsules may be in the form of hard capsules, for example hard gelatin capsules, or soft capsules which are prepared by conventional processes in which the active is incorporated in a carrier and encapsulated. Optionally, such dosages may include an enteric coating prepared according to conventional procedures which may be used to modify the release rate, or an excipient which delays release to provide a delayed release or a sustained release composition. Liquid dosage forms may be prepared by dissolving the active in a suitable liquid carrier such as water or an oily excipient, optionally in the presence of one or more dissolution agents, surfactants and/or suspending aids. Compositions for rectal administration are known pharmaceutical forms for such administration, for examples suppositories with a waxy or polyethylene glycol base. Compositions for parenteral administration are also known pharmaceutical forms for such administration, for examples sterile solutions or suspensions in a suitable solvent system.

Compositions for topical administration may include creams, lotions, ointments, gels or other such dosages which may be administered by applying the composition directly to the affected area or by incorporating the composition in a vehicle such as a transdermal patch or as a composition contained within a permeable membrane for application to a painful area. Conventional aqueous and non-aqueous carriers, such as mineral oils and waxes may be used alone or in combination to prepare creams, lotions or ointments. Gels may be prepared by mixing the compound of Formula 1 with a topical vehicle comprising a gelling agent, for example, Carbomer in the presence of water. Optionally further formulation aids such as transdermal accelerators, thickening agents may also be incorporated. In another embodiment, the compound of the invention may be used in combination with a suitable pharmaceutical excipient for the topical treatment of back pain. The combination of the compound and the pharmaceutical excipient may be in the form of a gel, the gel shaped and adapted for placement upon the skin of a subject in pain. In another embodiment, the combination of the compound and the pharmaceutical excipient may be incorporated within the fabric of a patch, the patch shaped and adapted for placement upon and/or adhesion to the skin of a subject in pain. In a more preferred embodiment the compound is released at a slow rate from the pharmaceutical excipient within fabric of the patch.

The compound of Formula 1 may be incorporated in pharmaceutical compositions which are useful in the conditions recited below.

The present disclosure contemplates that the compound of Formula 1 may be used in a clinical setting for the treatment of neuropathic pain. In another embodiment, the compound may be used for the treatment of pain in the central nervous system (CNS). In another embodiment, the compound of Formula 1 may be used for the treatment of pain which is not associated with the CNS. In a further embodiment, the compound of Formula 1 may be used for the treatment of pain which is associated with the peripheral nervous system (PNS). In yet another embodiment, the compound of Formula 1 may be used for the treatment of a CNS disorder. In one embodiment, the CNS disorder is selected from the group consisting of epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system including Down syndrome, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia. In another embodiment the compound of Formula 1 may be used in the treatment of pain in the CNS, such as, but not limited to, headache and migraine.

In another embodiment, the compound of Formula 1 may be used in combination with a suitable lotion in a pharmaceutical formulation for the topical treatment of back pain. In another embodiment, the compound of the invention may be used for the topical treatment of joint pain.

EXAMPLES

Optical Resolution of Compounds of Formulae 2a and 2b

Step 1

(1R,5S)-3-Ethylbicyclo[3.2.0]hept-3-en-6-one (2a)

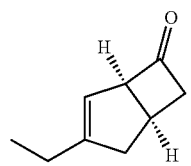

To a stirred solution of 4-pyridinecarboxaldehyde (59.29 g, 554 mmol) and 4-methylmorpholine (55.9 g, 553 mmol) in 1-methyl-2-pyrrolidinone (188 mL) at room temperature was added a racemic mixture of 3-ethylbicyclo[3.2.0]hept-3-en-6-one (WO2012169475) (75.34 g, 553 mmol), followed by a solution of (R)-2-(diphenylmethyl)pyrrolidine (13.11 g, 55.3 mmol) in 1-methyl-2-pyrrolidinone (37.7 mL). The mixture was stirred at 40° C. for 18 hours. The reaction mixture was allowed to cool to room temperature and then diethyl ether (960 mL) was added. The mixture was then washed with 1M HCl (2×820 mL), water (600 mL) and brine (600 mL). The organic layer was separated and dried over magnesium sulfate. The resulting solution was filtered and evaporated under reduced pressure (200 mbar, bath temp 28° C.) to afford 26.4 g of an oil. The aqueous phase was further extracted with isohexane (300 mL) which was subsequently washed with water (100 mL) and brine (100 mL). The resulting solution dried and evaporated as previously and the residue combined with the first batch of product to provide enantio-enriched (1R,5S)-3-ethylbicyclo[3.2.0]hept-3-en-6-one (28.8 g, 39%) as a colourless oil.

$^1$H NMR (300 MHz, CDCl$_3$): δ 5.21 (1H, m), 4.23-4.14 (1H, m), 3.30-3.12 (1H, m), 2.85-2.70 (3H, m), 2.38-2.25 (1H, m), 2.13 (2H, q, J=7.4), 1.06 (3H, t, J=7.4).

Determination of enantiomeric purity of the above product was performed by preparation of the corresponding 1,3-dioxolane derived from reaction between (1R,5S)-3-ethylbicyclo[3.2.0]hept-3-en-6-one and (2R,3R)-(−)-2,3-butanediol. Integration of $^1$H-NMR signals indicated that the enantiomeric excess (e.e.) was ≥98% and confirmed by GC-MS analysis as described below:

Determination of enantiomeric purity of (1R,5S)-3-ethylbicyclo[3.2.0]hept-3-en-6-one The two diastereioiomeric 1,3-dioxolanes derived from reaction between racemic (1RS,5RS)-3-ethylbicyclo[3.2.0]hept-3-en-6-one and (2R,3R)-(−)-2,3-butanediol were also synthesised.

By comparison and integration of $^1$H-NMR signals indicated that the enantiomeric excess (ee.) was ≥98%.

(1'R,4R,5R,5'S)-3'-ethyl-4,5-dimethyl-spiro[1,3-dioxolane-2,6'-bicyclo[3.2.0]hept-3-ene]

(Single Enantiomer)

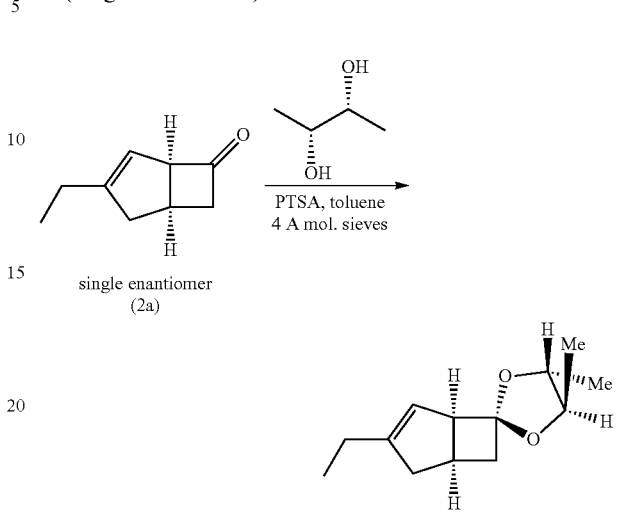

A stirred mixture of (1R,5S)-3-ethylbicyclo[3.2.0]hept-3-en-6-one (100 mg, 0.73 mmol), (2R,3R)-(−)-2,3-butanediol (131 mg, 1.46 mmol) and para-toluene sulfonic acid monohydrate (14 mg, 0.073 mmol) in toluene (2 mL) containing 4 A molecular sieves was heated at 120° C. for 1 hour. After cooling to room temperature the majority of the solvent was evaporated. The residue was purified by chromatography on silica (5% diethyl ether:isohexane) to afford (1'R,4R,5R, 5'S)-3'-ethyl-4,5-dimethyl-spiro[1,3-dioxolane-2,6'-bicyclo [3.2.0]hept-3-ene].

$^1$H NMR (300 MHz, CDCl$_3$): δ 5.33 (1H, m), 3.58-3.72 (2H, m), 3.37-3.43 (1H, m), 2.48-2.59 (3H, m), 2.05-2.20 (4H, m), 1.31 (3H, d, J=6.0), 1.25 (3H, d, J=6.0), 1.09 (3H, t, J=7.4).

Integration of $^1$H-NMR signals indicated that the enantiomeric excess (e.e.) was ≥98%. GC-MS (Hewlett-Packard 5972, HP-5MS 25M×0.25 mm×0.25 μm, helium carrier gas (GC oven temperature 60° C. for 1 min then gradient 60-300° C. over 24 min then 300° C. for 20 min). m/z (EI) 208 [M]$^+$ at 10.36 min.

(1'S,4R,5R,5'R)-3'-ethyl-4,5-dimethyl-spiro[1,3-dioxolane-2,6'-bicyclo[3.2.0]hept-3-ene] and (1'R,4R,5R,5'S)-3'-ethyl-4,5-dimethyl-spiro[1,3-dioxolane-2,6'-bicyclo[3.2.0]hept-3-ene] (1:1 mixture of two diastereoisomers)

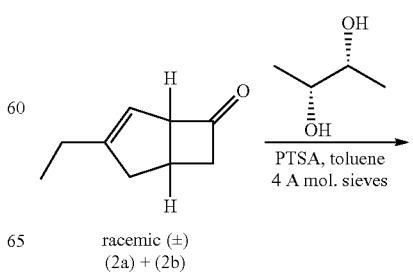

racemic (±)
(2a) + (2b)

-continued

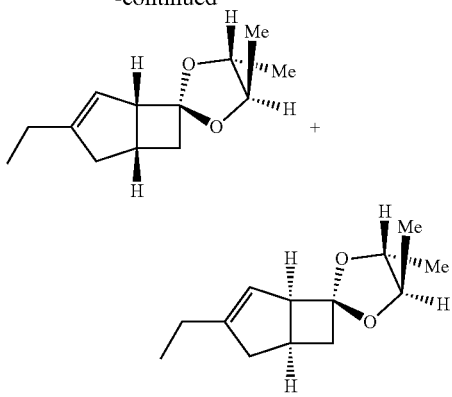

A stirred mixture of racemic (1RS,5RS)-3-ethylbicyclo[3.2.0]hept-3-en-6-one (100 mg, 0.73 mmol), (2R,3R)-(−)-2,3-butanediol (131 mg, 1.46 mmol) and para-toluene sulfonic acid monohydrate (14 mg, 0.073 mmol) in toluene (2 mL) containing 4 Å molecular sieves was heated at 120° C. for 1 hour. After cooling to room temperature the majority of the solvent was evaporated. The residue was purified by chromatography on silica (5% diethyl ether:isohexane) to afford a 1:1 mixture of (1'S,4R,5R,5'R)-3'-ethyl-4,5-dimethyl-spiro[1,3-dioxolane-2,6'-bicyclo[3.2.0]hept-3-ene] and (1R,4R,5R,5'S)-3'-ethyl-4,5-dimethyl-spiro[1,3-dioxolane-2,6'-bicyclo[3.2.0]hept-3-ene].

¹H NMR (300 MHz, CDCl₃): δ 5.37 (0.5H, m), 5.33 (0.5H, m), 3.58-3.72 (2H, m), 3.49-3.54 (0.5H, m) 3.37-3.43 (0.5H, m), 2.42-2.60 (3H, m), 2.02-2.21 (4H, m), 1.30-1.32 (3H, m), 1.23-1.26 (3H, m), 1.09 (3H, t, J=7.4).

Integration of ¹H-NMR signals indicated 1:1 ratio of diastereoisomers.

GCMS (Hewlett-Packard 5972, HP-5MS 25M×0.25 mm×0.25 μm, helium carrier gas (GC oven temperature 60° C. for 1 min then gradient 60-300° C. over 24 min then 300° C. for 20 min). m/z (EI) 208 [M]⁺ at 10.28 and 10.36 min (1:1 ratio of diastereoisomers).

Production of Compound of Formula 1

Step 2

(2E/Z)-2-((1R,5S)-3-Ethyl-6-bicyclo[3.2.0]hept-3-enylidene)acetonitrile (5)

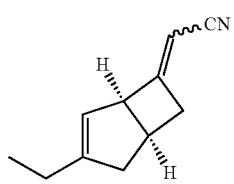

To a solution of 1M potassium tert-butoxide in tetrahydrofuran (179 mL, 179 mmol) at 0° C. was added diethyl cyanomethylphosphonate (33.19 g, 187 mmol). The reaction mixture was stirred at 0° C. for 10 minutes, allowed to warm to room temperature and stirred for a further 30 minutes. The mixture was transferred to a pressure equalising dropping funnel and added dropwise to a solution of (1R,5S)-3-ethylbicyclo[3.2.0]hept-3-en-6-one (product of step 1) (23.23 g, 170.6 mmol) in tetrahydrofuran (219.5 mL) at 0° C. The mixture was allowed to warm to room temperature and stirred for 18 hours.

The mixture was diluted with saturated aqueous ammonium chloride (200 mL) and ethyl acetate (400 mL) and the layers separated. The aqueous layer was extracted with ethyl acetate (3×100 mL) and the combined organic layers washed with saturated aqueous sodium bicarbonate solution (75 mL), brine (75 mL) and dried over magnesium sulfate. The residue after filtration and evaporation was checked by NMR and shown to contain ethyl phosphate by-products. The crude product was partitioned between isohexane (200 mL) and water (350 mL). The layers were separated and the aqueous re-extracted with isohexane (4×100 mL). The combined organic layers were dried over magnesium sulfate and evaporated to afford (2E/Z)-2-((1R,5S)-3-ethyl-6-bicyclo[3.2.0]hept-3-enylidene)acetonitrile as a ~60:40 mixture of E/Z isomers (31.3 g when combined with product derived from a preceding batch from 5.5 g starting material, 93%).

LCMS (Agilent, Waters SunFire C18, 4.6×30 mm, Acidic (0.05% formic acid, 6 min method, 3-97% acetonitrile/water): m/z 160.2 (M+H)⁺ (ES⁺) at 2.88 min.

¹H NMR (300 MHz, CDCl₃): ~60:40 mixture of alkene isomers δ 5.43 (0.4H, m), 5.23 (0.6H, m), 5.09 (0.6H, m), 4.98 (0.4H, m), 4.12 (0.4H, br s), 3.93 (0.6H, br s), 3.19-2.90 (2H, m), 2.74-2.46 (2H, m), 2.29-2.07 (3H, m), 1.14-1.06 (3H, m).

Step 3

2-01R,5S,6S)-3-Ethyl-6-(nitromethyl)bicyclo[3.2.0]hept-3-en-6-yl)acetonitrile (6)

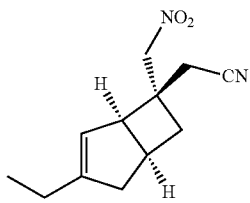 [SMILES: CCC1=C[C@@H]2[C@H](C1)C[C@@]2(CC#N)C[N+](=O)[O-]]

To a solution (2E/Z)-2-((1R,5S)-3-ethyl-6-bicyclo[3.2.0]hept-3-enylidene)acetonitrile (product of step 2) (31.2 g, 196 mmol) in nitromethane (273 mL, 307 g, 5.04 mol) under nitrogen was added 1,8-diazabicyclo[5.4.0]undec-7-ene (32 mL, 32.5 g, 213.4 mmol) and the mixture stirred for 18 hours at room temperature.

The reaction mixture was poured into a 5% aqueous solution of potassium dihydrogen orthophosphate (1270 mL) and ethyl acetate (950 mL) added. The layers were separated and the aqueous layer further extracted with ethyl acetate (2×400 mL). The combined organic layers were dried over magnesium sulfate and evaporated to afford a crude product. The residue was purified by chromatography on a pad of silica (35% ethyl acetate:isohexane) to afford 2-((1R,5S,6S)-3-ethyl-6-(nitromethyl)bicyclo[3.2.0]hept-3-en-6-yl)acetonitrile (38.38 g, 89% yield+less pure fraction 3.3 g) as a ~70:30 mixture of diastereomers. Data for major diastereomer: 2-((1R,5S,6S)-3-ethyl-6-(nitromethyl)bicyclo[3.2.0]hept-3-en-6-yl)acetonitrile.

LCMS (Agilent, Waters SunFire C18, 4.6×30 mm, Acidic (0.05% formic acid, 6 min method, 3-97% acetonitrile/water): m/z 221 (M+H)⁺ (ES⁺) at 2.81 min.

¹H NMR (300 MHz, DMSO-d₆): δ 5.33 (1H, m), 4.86 (2H, s), 3.16 (1H, br. s), 3.02-2.82 (1H, m), 2.65 (2H, s), 2.48-2.40 (1H, m), 2.23 (1H, ddd, J=12.4, 8.8, 2.5), 2.16-2.02 (3H, m), 1.56 (1H, dd, J=12.5, 7.2), 1.06 (3H, t, J=7.5) ppm.

Step 4

5-(((1R,5S,6S)-3-Ethyl-6-(nitromethyl)-6-bicyclo[3.2.0]hept-3-enyl)methyl)-1H-tetrazole (7)

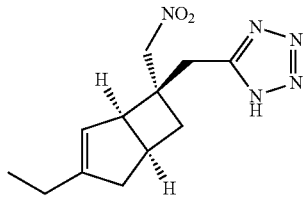 [SMILES: CCC1=C[C@@H]2[C@H](C1)C[C@@]2(Cc1nnn[nH]1)C[N+](=O)[O-]]

To a solution of 2-((1R,5S,6S)-3-ethyl-6-(nitromethyl)bicyclo[3.2.0]hept-3-en-6-yl)acetonitrile (product of step 3) (11 g, 50 mmol) in 1-methyl-2-pyrrolidinone (158 mL) was added triethylamine hydrochloride (26.55 g, 192 mmol) and sodium azide (12.54 g, 192 mmol). The flask was heated under nitrogen at 110° C. for 18 hours and then allowed to cool to room temperature. The mixture was diluted with water (200 mL) and carefully adjusted to pH 11-12 using aqueous 2M sodium hydroxide solution. The resulting solution was extracted with ethyl acetate (2×350 mL) and the organic layer back-extracted with aqueous 1M sodium hydroxide solution (2×40 mL). To the combined basic aqueous phases was added 20% aqueous sodium nitrite solution (100 mL) and the mixture cooled in an ice bath. 20% aqueous sulphuric acid was added dropwise (gas evolution) until the mixture was acidified and gas evolution ceased (~pH 1-2). The mixture was then stirred for a further 1 hour. The resulting aqueous solution was extracted with ethyl acetate (3×300 mL). The combined organic layers were washed with water (3×250 mL) and brine (2×100 mL) and dried over magnesium sulfate. Filtration and evaporation gave a crude product which was purified by chromatography on silica (ethyl acetate:isohexane:acetic acid 250:750:1) to afford (single diastereoisomer) 5-(((1R,5S,6S)-3-ethyl-6-(nitromethyl)-6-bicyclo[3.2.0]hept-3-enyl)methyl)-1H-tetrazole (4.7 g, 17.8 mmol, 35%) (and a further 0.5 g of a ~95:5 mixture of diastereomers for re-purification).

LCMS (Agilent, Waters SunFire C18, 4.6×30 mm, Acidic (0.05% formic acid, 6 min method, 3-97% acetonitrile/water): m/z 264 (M+H)⁺ (ES⁺); 262 (M−H)⁻ (ES⁻), at 2.38 min.

¹H NMR (300 MHz, DMSO-d₆): δ 16.10 (1H, br. s), 5.37 (1H, d, J=1.5), 4.79 (2H, s), 3.22 (1H, br. s), 3.02 (2H, s), 2.94-2.81 (1H, m), 2.48-2.40 (1H, m), 2.19-2.02 (4H, m), 1.64 (1H, dd, J=12.4, 7.5), 1.05 (3H, t, J=7.5) ppm.

Step 5

[(1R,5S,6S)-3-Ethyl-6-(1H-tetrazol-5-ylmethyl)-6-bicyclo[3.2.0]hept-3-enyl]methanamine (1)

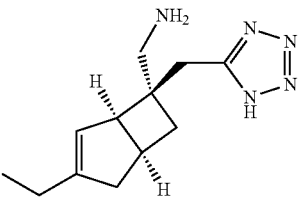 [SMILES: CCC1=C[C@@H]2[C@H](C1)C[C@]2(CN)Cc1nnn[nH]1]

To a solution of 5-(((1R,5S,6S)-3-ethyl-6-(nitromethyl)-6-bicyclo[3.2.0]hept-3-enyl)methyl)-1H-tetrazole (product of step 4) (1.377 g, 5.23 mmol) in ethanol (27.3 mL) under nitrogen was added concentrated hydrochloric acid (7.85 mL). Zinc dust (6.08 g, 93.5 mmol) was added portion-wise over 10 minutes (with external cooling in a water/ice-bath to ensure that the internal reaction temperature did not exceed 35° C.). The reaction mixture was stirred at room temperature for 18 hours. The reaction mixture was poured onto a 50 g SCX cartridge (pre-washed with methanol 200 mL) which was then eluted with methanol (160 mL), followed by aqueous methanol (1:1, 120 mL) and methanol (120 mL). The resin was then eluted with 0.7M ammonia in methanol solution (360 mL) and fractions collected. Fractions containing product were combined and evaporated to afford [(1R,5S,6S)-3-ethyl-6-(1H-tetrazol-5-ylmethyl)-6-bicyclo[3.2.0] hept-3-enyl] methanamine (1.159 g, 95%) as a white powder.

LCMS (Agilent, Waters SunFire C18, 4.6×30 mm, Acidic (0.05% formic acid, 6 min method, 3-97% acetonitrile/water): m/z 234 (M+H)⁺ (ES⁺); 232 (M−H)⁻ (ES⁻), at 0.86 min.

¹H NMR (400 MHz, CD₃OD): δ 5.42 (1H, br m), 3.08-3.15 (3H, m), 3.07 (1H, d, J=13), 3.03 (1H, d, J=16), 2.82 (1H, m), 2.54 (1H, br. dd, J=16, 8), 2.18 (2H, q, J=7), 2.10-2.16 (1H, br. d, J=16), 1.93 (1H, ddd, J=12, 9, 3), 1.63 (1H, dd, J=12, 7), 1.12 (3H, t, J=8) ppm.

NMR Assignment: (CD₃OD)

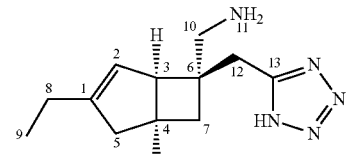

| Assignment | ¹H | | | ¹³C |
|---|---|---|---|---|
| | Chemical Shift (p.p.m) | Multiplicity | Integration | Chemical Shift (p.p.m) |
| 1 | | | | 151.6 |
| 2 | 5.42 | br m | 1 | 122.6 |
| 3 | ~3.08 | br m | 1 | 53.8 |
| 4 | 2.82 | m | 1 | 31.9 |
| 5 | 2.09, 2.51 | br d, br dd | 1, 1 | 43.0 |
| 6 | | | | 44.9 |
| 7 | 1.63, 1.93 | dd, m | 1, 1 | 37.0 |
| 8 | 2.18 | q | 2 | 25.4 |
| 9 | 1.12 | t | 3 | 12.9 |

-continued

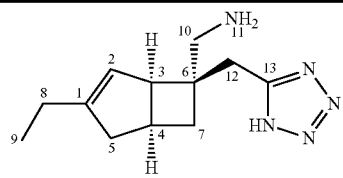

| Assignment | Chemical Shift (p.p.m) | ¹H Multiplicity | Integration | ¹³C Chemical Shift (p.p.m) |
| --- | --- | --- | --- | --- |
| 10 | 3.07, 3.13 | 2 * d | 2 | 48.2 |
| 12 | 2.96, 3.03 | 2 * d | 2 | 29.9 |
| 13 | | | | 159.9 |

Key to multiplicity abbreviations:
s = singlet,
d = doublet,
t = triplet,
q = quartet,
m = multiplet, (may be combined eg dd doublet of doublets or prefixed with br - broad e.g. br s broad singlet
Proton chemical shifts referenced to residual water at 4.90 p.p.m
Carbon chemical shifts referenced using the internal spectrometer referencing HPLC Purity: 99.3% (% AuC at 210 nm).
Column: Waters XBridge C18, 150×4.6 mm, 3.5μ
Solvent A: Water+0.1% TFA
Solvent B: Acetonitrile+0.1% TFA
Flow Rate: 1.0 ml/min
Temperature: 40° C.
Injection vol: 5 μl of a 1 mg/ml solution in Acetonitrile/Water (1:1)
UV Wavelength: 210 nm
Solvent Gradient:

| Time (Mins) | Solvent A (%) | Solvent B (%) |
| --- | --- | --- |
| 0 | 100 | 0 |
| 3 | 100 | 0 |
| 23 | 50 | 50 |
| 28 | 50 | 50 |
| 29 | 100 | 0 |
| 32 | 100 | 0 |

Retention Time: ca. 15.7 mins
Chiral HPLC purity: >99.9%.
Column: Daicel Chiralpak IC, 250×4.6 mm, 5μ
Mobile Phase: Iso-hexane: Ethanol (70:30)
Run Conditions: Isocratic analysis, 30 minute runtime
Flow Rate: 1.5 ml/min
Temperature: Ambient
Injection Volume: 10 μl of a 0.5 mg/ml solution in Ethanol
UV Wavelength: 215 nm
Retention Time: Desired isomer elutes at ca. 20 mins
Undesired isomer elutes at ca. 10 mins
Optical Rotation: $[\alpha]_D^{23}$ −101.5 (c=27.4 mg in EtOH (2 mL))
Melting Point: 203-206° C.

Alternative Procedure for Reduction of Nitro-Group (Step 5) Exemplified on Racemic Mixture Racemic [(1R,5S,6S)-3-Ethyl-6-(1H-tetrazol-5-ylmethyl)-6-bicyclo[3.2.0]hept-3-enyl]methanamine To a solution of racemic 5-(((1R,5S,6S)-3-ethyl-6-(nitromethyl)-6-bicyclo[3.2.0]hept-3-enyl)methyl)-1H-tetrazole (275 mg, 1.04 mmol) in ethanol (2.2 mL) under nitrogen was added hydrazine hydrate (201 μL, 207 mg, 4.13 mmol). Raney Nickel slurry in water (67 μL) was added and the mixture stirred at room temperature for 1 hour. An additional aliquot of Raney Nickel slurry (100 μL) and hydrazine hydrate (200 μL) was added and the mixture stirred for a further 18 hours. A further aliquot of Raney Nickel slurry (200 μL) and hydrazine hydrate (200 μL) was added and the mixture stirred for a further 2 hours after which time the reaction mixture was filtered through celite and washed with ethanol. The resulting solution was evaporated and purified on an SCX cartridge eluting with methanol. The resin was then eluted with 0.7M ammonia in methanol solution and fractions collected. Fractions containing product were combined and evaporated to afford racemic [(1R,5S,6S)-3-ethyl-6-(1H-tetrazol-5-ylmethyl)-6-bicyclo[3.2.0]hept-3-enyl] methanamine (216 mg, 89%).

LCMS and ¹H-NMR data as reported in step 5 above.

The invention claimed is:

1. A process to isolate a compound of Formula 2a

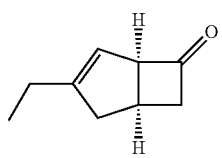

Formula 2a or a salt or solvate thereof, comprising
a) reacting a mixture of diastereoisomers of Formulae 2a, 2b

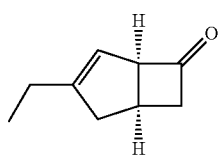

Formula 2a

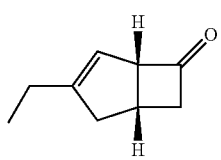

Formula 2b with a basic heterocyclic-aldehyde compound and an optically active amine in the presence of a base; and
b) separating the compound of Formula 2a from the product of step a) by acid extraction.

2. A process according to claim 1 wherein the compound of Formula 2a is produced with an enantiomeric excess of 98%.

3. A process according to claim 1, wherein the basic heterocyclic-aldehyde compound is a compound of Formula 12

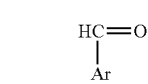

Formula 12 in which Ar represents a heterocyclic 5- or 6-membered heteroaryl ring structure, optionally substituted by one or two substituents selected from $C_{1-6}$ alkyl and $C_{1-6}$ alkoxy.

4. A process according to claim 3, wherein the basic heterocyclic-aldehyde compound of Formula 12 is selected from the group consisting of 4-pyridinecarboxalaldehyde, 1-methyl-5-imidazolecarboxaldehyde, 1-methyl-4-imidazolecarboxaldehyde, 3-pyridinecarboxaldehyde and 2-pyridine-carboxaldehyde.

5. A process according to claim 4, wherein the basic heterocyclic-aldehyde compound comprises 4-pyridinecarboxyaldehyde.

6. A process according to claim 1, wherein the optically active amine is a secondary amine.

7. A process according to claim 6, wherein the optically active amine comprises (R)-2-(diphenylmethyl)pyrrolidine.

8. A process according to claim 1, wherein the base is selected from the group consisting of 4-methylmorpholine, N,N-diisopropylethylamine, trimethylamine, tributylamine, N-methylpyrrole, N-methylpyrolidine, N-methylpiperadine, pyridine, 4-picoline, 2,6-lutidine, N-methylimidazole, N,N-diethylaniline, potassium phosphate and 1,8-diazobicyclo[5,4,0]undec-7-ene and 1,4-diazobicyclo[2,2,2]octane.

9. A process according to claim 8, wherein the base comprises 4-methylmorpholine.

10. A process according to claim 1, wherein the stoichiometric ratio of the basic heterocyclic-aldehyde compound to the mixture of diastereoisomers of Formulae 2a, 2b is in the range 0.5:1 to 2:1.

11. A process according to claim 1, wherein the reaction between the mixture of diastereoisomers of Formulae 2a, 2b and the basic heterocyclic-aldehyde compound and optically active amine is conducted over a period of 15 to 24 hours, at a temperature in the range from 30 to 60° C.

12. A process according to claim 1, wherein the stoichiometric ratio of the optically active amine to the mixture of diastereoisomers of Formulae 2a, 2b is in the range 0.01:0.3.

13. A process according to claim 1, wherein the reaction between the mixture of diastereoisomers of Formulae 2a, 2b and the basic heterocyclic-aldehyde compound and optically active amine is carried out in the presence of a solvent.

14. A process according to claim 13, wherein the solvent comprises 1-methyl-2-pyrrolidinone.

15. A process according to claim 1, wherein the acid extraction is carried out with hydrochloric acid in the presence of a solvent and water.

16. A process according to claim 1, wherein the mixture of diastereoisomers of Formulae 2a, 2b is a racemic mixture.

17. A process according to claim 1, wherein the reaction product of the mixture of diastereoisomers of Formulae 2a, 2b with the basic heterocyclic-aldehyde compound of Formula 13

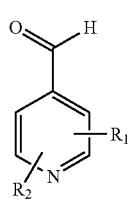

Formula 13 in which $R_1$ represents hydrogen or $C_{1-6}$ alkyl and $R_2$ represents hydrogen or $C_{1-6}$ alkoxy, and an optically active amine, is a mixture of compounds of Formula 14

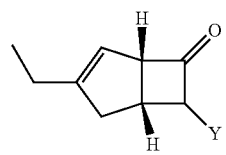

Formula 14 in which Y is =CH-(4-pyridyl) or CH(OH)-(4-pyridyl).

18. A process to prepare a compound of Formula 1

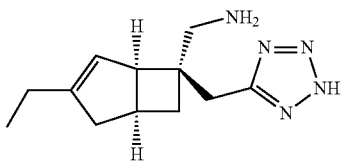

Formula 1 or a pro-drug thereof, comprising the step of resolving a mixture of diastereoisomers of Formulae 2a, 2b

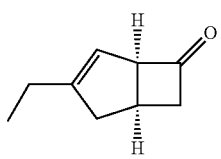

Formula 2a

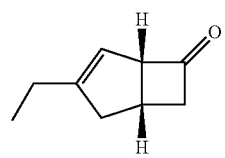

Formula 2b into a compound of Formula 2a

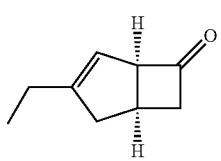

Formula 2a by reaction with a basic heterocyclic-aldehyde compound in the presence of an optically active amine and a base and separating out the compound of Formula 2a, followed by conversion of a compound of Formula 2a to a compound of Formula 1.

19. A process to prepare a compound of formula 1 according to claim 18, wherein said conversion comprises reacting a compound of Formula 2a

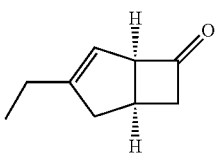

Formula 2a with a double bond-forming reagent in the presence of a base to prepare a compound of Formula 5

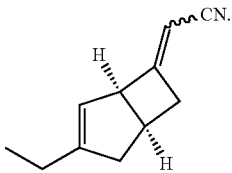

Formula 5

20. A process to prepare a compound of Formula 1 according to claim 19, wherein said conversion further comprises reacting a compound of Formula 5

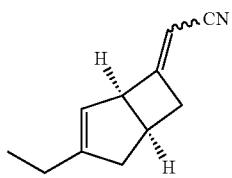

Formula 5 with nitromethane in the presence of a base to prepare a compound of Formula 6

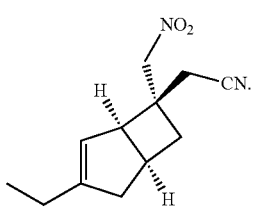

Formula 6

21. A process to prepare a compound of Formula 1 according to claim 20, wherein said conversion further comprises reacting a compound of Formula 6

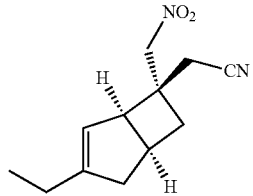

Formula 6 optionally in the presence of a catalyst and at elevated temperature, to prepare a compound of Formula 7

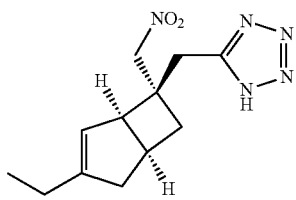

Formula 7

22. A process to prepare a compound of Formula 1 according to claim 21, wherein said conversion further comprises reducing a compound of Formula 7

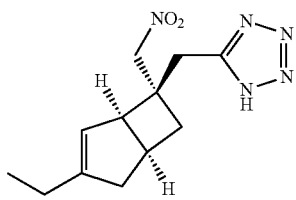

Formula 7 to prepare the compound of Formula 1

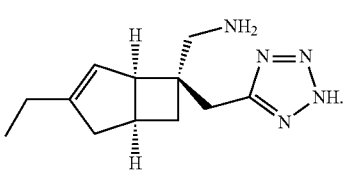

Formula 1

23. A process according to claim 18, wherein the pro-drug is a hydrolysable carbamate of the amine group of compounds of Formula 1.

* * * * *